United States Patent [19]

Engelhardt et al.

[11] Patent Number: 5,027,793
[45] Date of Patent: Jul. 2, 1991

[54] SURGICAL RETRACTOR

[75] Inventors: John A. Engelhardt; Jon C. Serbousek, both of Warsaw, Ind.; Wayne Paprosky, Glen Ellyn, Ill.

[73] Assignee: Boehringer Mannheim Corp., Indianapolis, Ind.

[21] Appl. No.: 502,190

[22] Filed: Mar. 30, 1990

[51] Int. Cl.$^5$ ............................................. A61B 17/02
[52] U.S. Cl. ...................................... 128/20; 606/53; 128/3
[58] Field of Search ...................... 128/20, 71, 72, 73, 128/3; 606/53, 54, 96, 104, 60

[56] References Cited

U.S. PATENT DOCUMENTS

| | | |
|---|---|---|
| 1,930,404 | 10/1933 | Wagner . |
| 2,236,067 | 3/1941 | Poth . |
| 2,301,500 | 11/1942 | Anderson . |
| 2,863,444 | 12/1958 | Winsten . |
| 3,364,919 | 1/1968 | Hunnicutt . |
| 3,731,673 | 5/1973 | Halloran ............................. 128/20 |
| 3,749,088 | 7/1973 | Kohlmann . |
| 4,570,624 | 2/1986 | Wu . |
| 4,610,243 | 9/1986 | Ray . |
| 4,686,972 | 8/1987 | Kurland . |
| 4,719,907 | 1/1988 | Banko et al. . |
| 4,747,395 | 5/1988 | Brief ..................................... 128/20 |
| 4,867,139 | 9/1989 | Girzadas ............................. 128/20 |

FOREIGN PATENT DOCUMENTS 1274432  5/1972  United Kingdom .................. 606/53

Primary Examiner—Stephen C. Pellegrino
Assistant Examiner—Glenn K. Dawson
Attorney, Agent, or Firm—Perman & Green

[57] ABSTRACT

A surgical retractor is disclosed for use when surgery is performed adjacent a bone and remains in place for an appropriate duration without requiring manual assistance. A barrier member includes a plurality of cannulated fixation posts for its temporary placement on, and attached to, the bone and a soft tissue engaging surface which extends transverse of a surface of the bone. Guides, including the cannulated fixation posts, slidably receive mounting pins which supplement the fixation posts for temporarily attaching the barrier member to the bone. The barrier member is also provided with bottom and top flanges which extend transversely of the soft tissue engaging surface and cooperate therewith to prevent entry of the soft tissue into an adjacent surgical site.

13 Claims, 2 Drawing Sheets

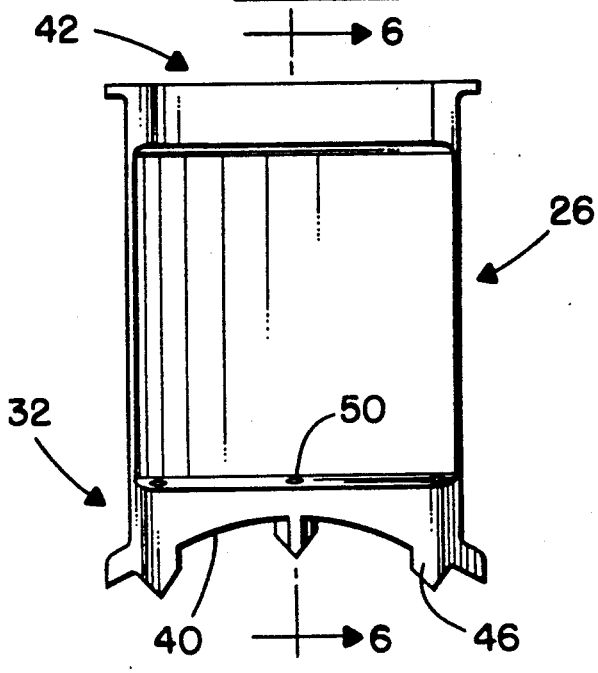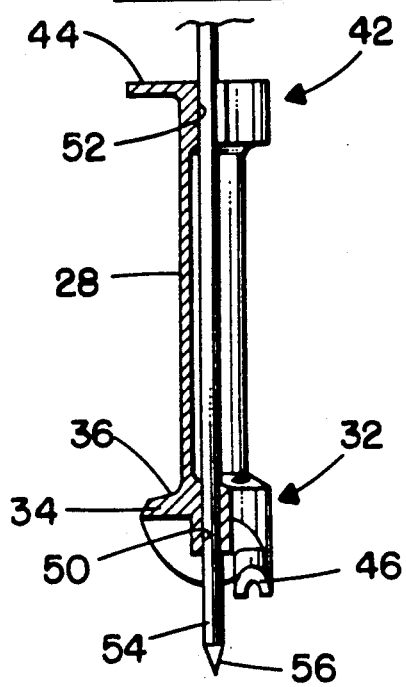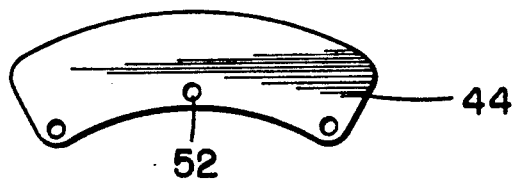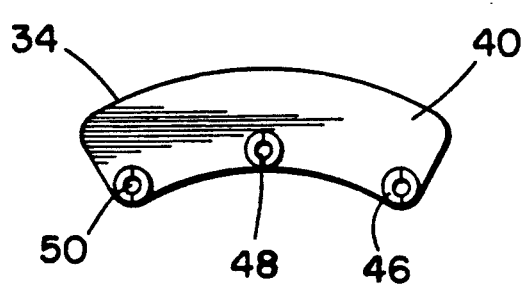

SURGICAL RETRACTOR

BACKGROUND OF THE INVENTION

1. Field of the Invention:

The present invention relates generally to surgical instruments and, more particularly, to surgical retractors for drawing and holding soft tissue away from the operative field during a surgical procedure.

2. Description of the Prior Art:

In surgical procedures, it is necessary to hold the edges of an incision apart to provide a clear operating field within which the surgeon can operate. Retractor devices for this purpose have long been used but have typically required one or more surgical attendants on a continuous basis to either hold them or closely monitor their function. One construction known to the prior art is presented in U.S. Pat. No. 3,749,088 to Kohlman. This patent discloses retractor apparatus which overlies the operative field and utilizes a plurality of opposed retractor units. The retractor units are adjustably mounted on a frame and act together to engage the tissue at the edges of the incision to draw it away from the operative field and expose it for an ensuing surgical procedure.

In a similar manner, U.S. Pat. No. 3,364,919 to Hunnicutt overlies the operative field and uses an elongated rectangular sheet metal strap of a chosen size and contour for engaging the edge of the incision.

A retractor of specialized design, intended specifically, for a gall bladder operation, is disclosed in U.S. Pat. No. 2,863,444 to Winsten. In this instance, the retractor is required to be held continuously by hand during surgery to draw the patient's liver away from the operative field.

None of the foregoing patents discloses a construction which is intended for, or renders possible, either temporary or permanent fixation to an underlying bone. While some previously known constructions of retractors were intended to engage an underlying bone, they were not temporarily or semi-permanently affixed to the bone. One instance is disclosed in U.S. Pat. No. 4,610,243 to Ray. In this instance, a retractor is provided which is said to be particularly useful for spinal surgery and comprises a malleable metal band one end of which is formed with rigid metal spikes intended for engagement with the underlying bone. The spikes do not appreciably penetrate the bone, only to the extent to provide a fulcrum enabling the band to engage the edge of the incision and draw back the soft tissue away from the operative field when a weight is applied to an opposite hooked end of the band.

Also known is U.S. Pat. No. 4,686,972 to Kurland which is a combination retractor and guide for a boring tool. An elongated main body has one end serrated for engagement with the bone to be drilled. The other end of the retractor is apertured for reception of the fingers of a surgical attendant and must be held throughout the drilling procedure to deflect any tissue which would otherwise interfere with the process.

While the patents to Ray and Kurland disclose retractors which are engageable with a bone, they do not provide for temporarily, but immovably, mounting the retractor to the bone. In each instance, which is typical of the prior art, the retractor must be held by a surgical attendant during the entire course of the surgical procedure requiring its use.

Thus, a significant drawback of the prior art resides in the need for surgical attendants in the operating room to substantially continuously hold, or closely monitor the use of, a surgical retractor.

SUMMARY OF THE INVENTION

It was with knowledge of the prior art as just described that the present invention was conceived and has now been reduced to practice. To this end, a surgical retractor has been devised which is intended for use when surgery is performed adjacent a bone. The retractor remains in place for as long as needed during the surgical procedure without requiring manual assistance.

In one instance, the surgical retractor of the invention may be used to hold and retain the abductor muscles and other soft tissue folded away in a superior direction from the acetabulum. The barrier member is illustrated and generally described as being of a curved one piece construction although it may be comprised of more than one piece should that prove to be desirable. In any event, it is intended to be temporarily or semi-permanently mounted to the ilium. The terms temporarily or semi-permanently are intended to indicate that it is not necessary for a surgical attendant to continuously hold the retractor in order for it to perform its function. The surgical retractor of the invention includes a plurality of cannulated fixation posts each having a terminal spike for piercing engagement with the ilium. Each fixation post includes a top guide bore for slidably receiving a mounting pin therein. Each top guide bore cooperates with a bottom guide bore formed in the barrier member at a location distant from the bone. The bottom guide bore also slidably receives the mounting pin and, with the top guide bore, guides the pin for movement between a first position disengaged from the bone and a second position engaged with the bone for removably attaching the barrier member to the bone. After one or more of the pins extending through their associated guide bores of the barrier member have become affixed to the bone, the barrier member will maintain its position relative to the bone until subsequently removed. The barrier member is also provided with bottom and top flanges which extend transversely of the soft tissue engaging surface and cooperate therewith to prevent entry of the soft tissue into an adjacent surgical site. The bottom flange of the barrier member has a generally planar impact surface whereby a suitable mallet or other impact tool can drive the fixation posts into the bone. Additionally, the top flange is formed with a curved bone engaging surface which is generally contoured to generally conform to the shape of the bone when it is seated thereon.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIG. 5 is a front elevation view of the invention;

FIG. 6 is a cross section view taken generally along line 6—6 in FIG. 5;

FIG. 7 is a top plan view of the invention; and

FIG. 8 is a bottom plan view of the invention.

DETAILED DESCRIPTION OF THE PREFERRED EMBODIMENT

Figure 1:
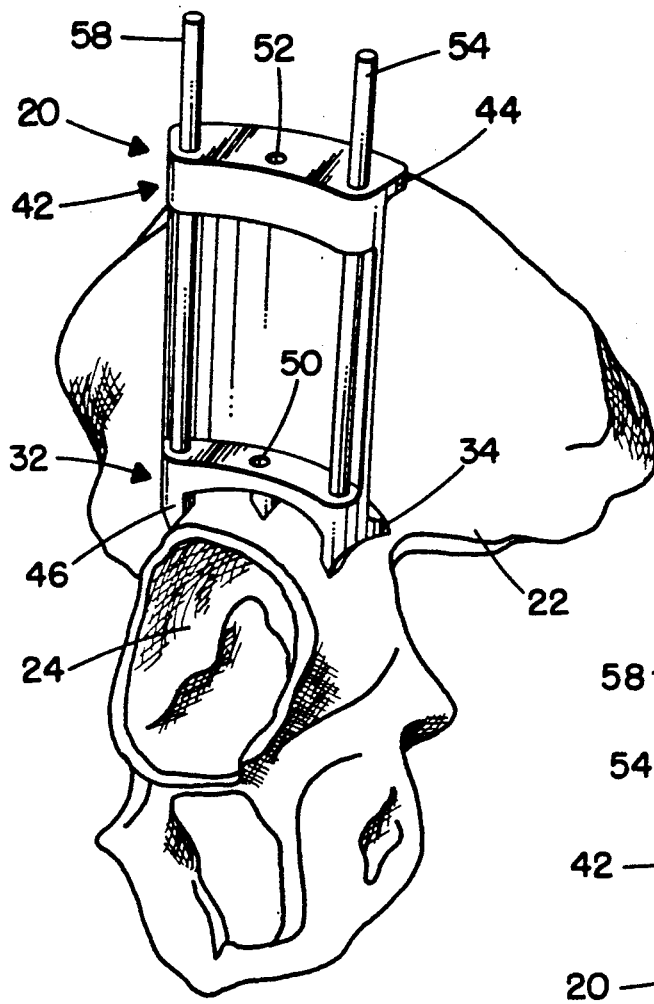
FIG. 1 is a front perspective view illustrating the surgical retractor of the invention in a typical application in engagement with the ilium bone superior to the acetabulum.
Figure 2:
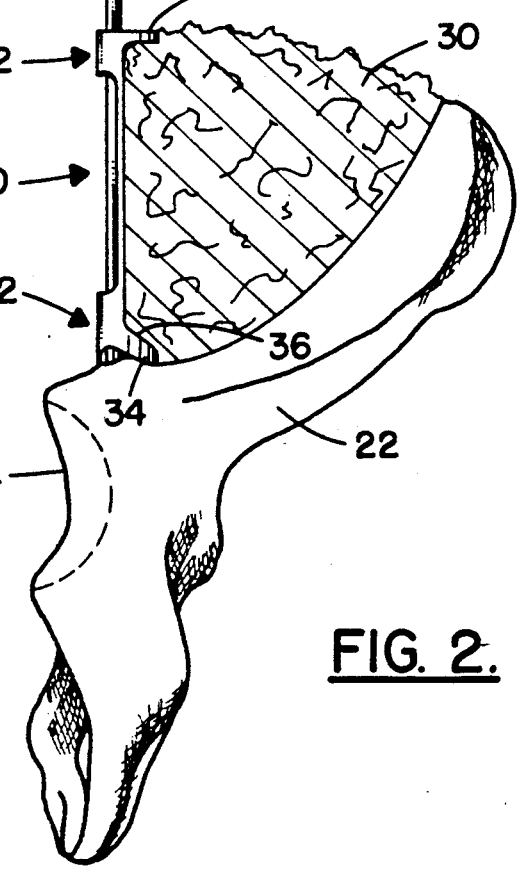
FIG. 2 is a side elevation view of the surgical retractor mounted to the ilium bone as in FIG. 1 and holding and containing the abductor muscles and other soft tissue away in a superior direction from the acetabulum.

Turn now to the drawings and, initially, to FIGS. 1 and 2, which illustrate a surgical retractor 20 embodying the invention and illustrating one typical use for the invention. That is, the surgical retractor 20 is illustrated as being temporarily or semi-permanently mounted on ilium bone 22 at a location superior to the acetabulum 24. However, it must be stressed that the invention need not be restricted to uses relating only to hip surgery, but that the surgical retractor 20 may indeed be used in any surgical procedure during which it is desirable or necessary to contain or hold soft or even hard tissue from an underlying operative field which is bone. Nonetheless, the use of a surgical retractor 20 depicted in FIGS. 1 and 2 is particularly useful for describing the invention.

The surgical retractor 20 includes a barrier member 26 which is provided with a soft tissue engaging surface 28, illustrated as lying in a convexly curved plane. It will be appreciated that while the convexly curved surface 28 is desirable for purposes of the use of the surgical retractor 20 illustrated in FIGS. 1 and 2, it may have a variety of other contours including a flat surface, or even a concave surface as might be desirable or necessary for other purposes. In any event, the soft tissue engaging surface 28 is seen in FIG. 2 as clearly shown engaging abductor muscles and other soft tissue 30 and holding them away from a site such as the acetabulum 24.

Figure 3:
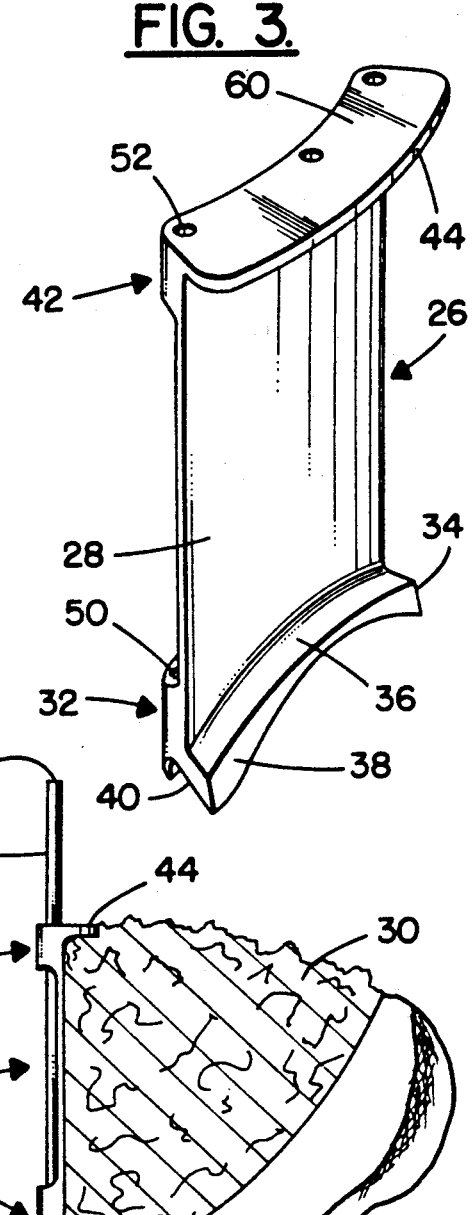
FIG. 3 is a perspective view of the surgical retractor of the invention, primarily illustrating its rear side.
Figure 4:
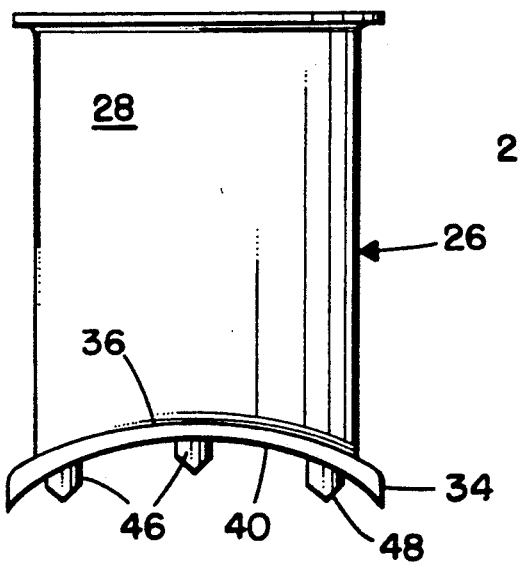
FIG. 4 is a rear elevation view of the invention.

The surgical retractor 20 also includes a top member 32 integral with the barrier member 26 which is engageable with the bone. More particularly, the top member 32 includes an integral top flange 34 which lies generally in a plane transverse of the soft tissue engaging surface 28. The top flange is more specifically defined by an arcuate shelf surface 36, a beveled surface 38, and a bone engaging surface 40 (FIGS. 3 and 4). The bone engaging surface 40 is contoured to generally conform to the shape of the underlying bone.

The surgical retractor 20 also includes a bottom member 42 integral with the barrier member 26. A bottom flange 44 is integral with the barrier member 26 adjacent the bottom guide member 42 and lies in a plane transverse of the soft tissue engaging surface 28. It cooperates with the top flange 34 to receive and hold the soft tissue 30 and prevent its entry into an adjacent surgical site, in the manner depicted in FIG. 2. The top member 32 includes a plurality of downwardly extending cannulated fixation posts 46 (see especially FIGS. 1, 4, 5, 6, and 8), each of which is provided with a terminal spike 48 for piercing engagement with the bone. Each fixation post has a top guide bore 50 therethrough. In a similar fashion, the bottom member 42 has a plurality of longitudinally extending bottom guide bores 52 therein which are generally aligned with the top guide bores 50 in the top member 32. While three sets of the guide bores 50, 52 are illustrated, and while that is a preferred number, the invention is not to be limited to that number. Each associated pair of guide bores 50, 52 serves to slidably receive an elongated mounting pin 54 which extends between a pointed active end 56 (FIG. 6) and a passive end 58 (FIGS. 1 and 2) adapted to be engaged by an impact tool.

In the course of a surgical procedure for which use of a surgical retractor is intended, an appropriate incision is made through the soft tissue. In the instance illustrated in FIGS. 1 and 2, the soft tissue is elevated from the superior acetabulum and the retractor 20 is inserted into the superior aspect of the acetabulum. This is accomplished by sliding the beveled surface 38 of the retractor underneath the soft tissue 30 so as to include the abductor muscles. When it is appropriately positioned as indicted in FIGS. 1 and 2, a generally planar impact surface 60 on the bottom flange 44 is tapped with a mallet or other suitable impact tool, so as to drive the terminal spikes 48 into embedded engagement with a bone 22. While such initial fixation is acceptable for proper placement of the surgical retractor 20, it is not generally sufficient for the duration of the surgical procedure. For this purpose, then, it is desirable to use one or more mounting pins 54, driving them into the exterior cortical wall of the bone.

In this fashion, the abductor muscles and other soft tissue 30 are generally contained against the soft tissue engaging surface 28 and between the top flange 34 and bottom flange 44, thereby providing excellent exposure of the acetabulum for the surgeon.

Upon completion of the surgical procedure, a surgical attendant can grip the bottom member 42 and the bottom flange 44 and draw the barrier member 26 in a direction away from the bone 22 and out of engagement therewith. Thereafter, the mounting pin or pins 54 which were utilized to hold the barrier member 26 in position can also be similarly removed. In the alternative, the mounting pin or pins 54 can be removed first and, thereafter, the barrier member 26.

While preferred embodiments of the invention have been disclosed in detail, it should be understood by those skilled in the art that various other modifications may be made to the illustrated embodiments without departing from the scope of the invention as described in the specification and defined in the appended claims. For example, while material has been removed between the bottom and top members 42, 32 for reasons of economy and lightness, the surgical retractor 20 may be of solid construction such that there would be no interruption between bores 50 and 52.

What is claimed is:

1. A surgical retractor for engaging and holding soft tissue away from a surgical site at or adjacent to a bone comprising:
   a barrier member including a soft tissue engaging surface; and
   a top member integral with said barrier member, said top member being contoured along its length to generally conform to the shape of the bone, said top member engageable with the bone and including first elongated fixation means extending therefrom having a first longitudinal axis for releasably attaching said barrier member to the bone.

2. A surgical retractor as set forth in claim 1 wherein said guide means includes;

a bottom guide member integral with said barrier member and distant from the bone when said barrier member is attached to the bone, said bottom guide member having a bottom bore therethrough;

a top guide member generally parallel to and spaced from said bottom guide member, said top guide member being integral with said barrier member and proximate the bone when said barrier member is attached to the bone, said top guide member having a top bore therethrough coaxial with the bottom bore in said bottom guide member; and wherein said second fixation means includes an elongated mounting pin slidably received by the bottom bore and by the top bore and extending between an active end engageable with the bone and a passive end adapted to be engaged by an impact tool.

3. A surgical retractor as set forth in claim 1 wherein said soft tissue engaging surface is in a convexly curved plane which is transverse to the outer surface of the bone.

4. A surgical retractor as set forth in claim 3 including:

a bottom flange integral with said barrier member adjacent said bottom guide member and lying in a plane transverse of said soft tissue engaging surface; and a top flange integral with said barrier member adjacent said top guide member and lying in a plane transverse of said soft tissue engaging surface and generally parallel to and spaced from said bottom flange;

said bottom flange and said top flange being mutually cooperable with said soft tissue engaging surface to receive and hold the soft tissue and prevent its entry into an adjacent surgical site.

5. A surgical retractor as set forth in claim 4 wherein said bottom flange includes a generally planar impact surface lying in a plane generally transverse to that of said soft tissue engaging surface.

6. A surgical retractor as set forth in claim 5 wherein said top flange includes a bone engaging surface contoured to generally conform to the shape of the bone and lying in a plane generally transverse to that of said soft tissue engaging surface.

7. A surgical retractor as set forth in claim 1 including:

second elongated fixation means adjacent said first fixation means, for releasably attaching said barrier member to the bone;

a bottom member integral with said barrier member and including bottom guide means;

said top member including top guide means spaced from said bottom guide means;

said second fixation means being slidably engageable with said bottom guide means and with said top guide means for movement between a first position disengaged from the bone and a second position engaged with the bone for removably attaching said barrier member to the bone.

8. A surgical retractor as set forth in claim 1 wherein said first fixation means includes a plurality of cannulated fixation posts having axes lying in a plane which is generally parallel to said soft tissue engaging surface, each of said fixation posts having a terminal spike for piercing engagement with the bone and a top guide bore therethrough;

wherein said barrier member includes:

a guide member integral with said barrier member, said guide member having a guide bore therethrough generally parallel with the first longitudinal axis; and including;

second fixation means slidably engageable with said guide member for movement between a first position disengaged from the bone and a second position engaged with the bone for releasably attaching said barrier member to the bone.

9. A surgical retractor as set forth in claim 8 wherein said second fixation means includes an elongated mounting pin slidably received by the bottom guide bore and by the top guide bore and extending between an active end piercingly engageable with the bone and a passive end adapted to be engaged by an impact tool.

10. A surgical retractor as set forth in claim 9 including:

a bottom flange integral with said barrier member adjacent said bottom guide member and lying in a plane transverse of said soft tissue engaging surface; and a top flange integral with said barrier member adjacent said top member and lying in a plane transverse of said soft tissue engaging surface and generally parallel to and spaced from said bottom flange;

said bottom flange and said top flange being mutually cooperable with said soft tissue engaging surface to receive and hold the soft tissue and prevent its entry into an adjacent surgical site.

11. A surgical retractor as set forth in claim 10 wherein said bottom flange includes a generally planar impact surface lying in a plane generally transverse to that of said soft tissue engaging surface.

12. A surgical retractor as set forth in claim 11 wherein said top flange includes a bone engaging surface contoured to generally conform to the shape of the bone and lying in a plane generally transverse to that of said soft tissue engaging surface.

13. A surgical retractor as set forth in claim 9 wherein said soft tissue engaging surface is in a convexly curved plane which is transverse to the outer surface of the bone.

* * * * *

UNITED STATES PATENT AND TRADEMARK OFFICE
CERTIFICATE OF CORRECTION

PATENT NO. : 5,027,793
DATED : July 2, 1991
INVENTOR(S) : Engelhardt et al

It is certified that error appears in the above-indentified patent and that said Letters Patent is hereby corrected as shown below:

In Claim 1, Col 4, line 67, before the "." insert the following paragraphs:

--second elongated fixation means adjacent said first fixation means, said second fixation means having a second longitudinal axis generally parallel to said first longitudinal axis for releasably attaching said barrier member to the bone; and guide means for slidably receiving said second fixation means, said second fixation means being movable between a first position disengaged from the bone and a second position engaged with the bone for attaching said barrier member to the bone--;

UNITED STATES PATENT AND TRADEMARK OFFICE
CERTIFICATE OF CORRECTION

PATENT NO. : 5,027,793
DATED : July 2, 1991
INVENTOR(S) : Engelhardt et al

It is certified that error appears in the above-indentified patent and that said Letters Patent is hereby corrected as shown below:

In Claim 4, Col. 5, line 26 delete "bottom";

In Claim 4, Col. 5, line 30 delete "guide";

In Claim 8, Col. 6, line 8 delete the semicolon ";" and insert a colon --:--.

Signed and Sealed this

Eighth Day of February, 1994

*Attest:*

BRUCE LEHMAN

*Attesting Officer*     Commissioner of Patents and Trademarks